United States Patent
Melendez et al.

(10) Patent No.: US 6,191,847 B1
(45) Date of Patent: *Feb. 20, 2001

(54) FIXED OPTIC SENSOR SYSTEM AND DISTRIBUTED SENSOR NETWORK

(75) Inventors: Jose L. Melendez, Plano; Richard A. Carr; Patrick Paul Smith, both of Rowlett; Dwight U. Bartholomew, Dallas; John H. Berlien, Jr., Plano; Frederick F. Geyer, Richardson; Paul S. Breedlove, McKinney, all of TX (US)

(73) Assignee: Texas Instruments Incorporated, Dallas, TX (US)

(*) Notice: Under 35 U.S.C. 154(b), the term of this patent shall be extended for 0 days.

This patent is subject to a terminal disclaimer.

(21) Appl. No.: 09/246,063

(22) Filed: Feb. 8, 1999

Related U.S. Application Data

(63) Continuation of application No. 08/942,563, filed on Oct. 1, 1997, now Pat. No. 5,946,083.
(60) Provisional application No. 60/027,187, filed on Oct. 2, 1996.

(51) Int. Cl.[7] .................................................. G01N 21/00
(52) U.S. Cl. ............................. 356/73; 356/39; 356/317
(58) Field of Search ............................... 356/73, 39, 317

(56) References Cited

U.S. PATENT DOCUMENTS

| | | |
|---|---|---|
| 5,268,304 | 12/1993 | Inman et al. . |
| 5,299,141 | 3/1994 | Hungerford et al. . |
| 5,357,441 | 10/1994 | Petty et al. . |
| 5,485,277 | 1/1996 | Foster . |
| 5,553,094 | 9/1996 | Johnson et al. . |
| 5,582,170 | 12/1996 | Soller . |

OTHER PUBLICATIONS

Melendez et al., A commercial solution for surface plasmon sensing, *Sensors and Actuators B*, vol. 35, No. 1/03, Sep. 1996, pp. 212–216.

*Primary Examiner*—Frank G. Font
*Assistant Examiner*—Reginald A. Ratliff
(74) *Attorney, Agent, or Firm*—David Denker; Wade James Brady, III; Frederick J. Telecky, Jr.

(57) ABSTRACT

A fixed optic sensor system (200) comprising a sensor system (210), and electronic sub-system (205) and a communications means (215). The system can be used for detecting the presence of various sample (236) properties and in that regard has widespread application by leveraging off various miniaturized sensor configurations including surface plasmon resonance (50), fluorescence (80), light transmission (125) and others (150). In one embodiment, the communications means (215) is a wireless transmitter/receiver. In another embodiment, a hand held instrument (358) can be used on-site and communicates with the sensor (350) to receive sample (352) related data and transmit it to a remote processing system (370) for further analysis. In yet another embodiment, a hand held instrument (403) has a plurality of cardiac marker binding ligands (400) deposited on the sensor/sample interface providing a medical diagnosis and point-of-care device (403).

19 Claims, 7 Drawing Sheets

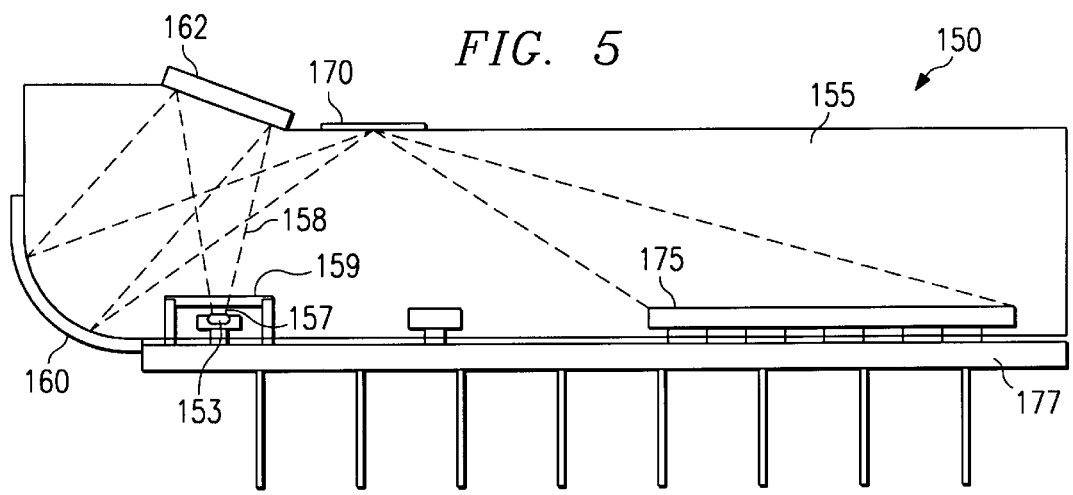
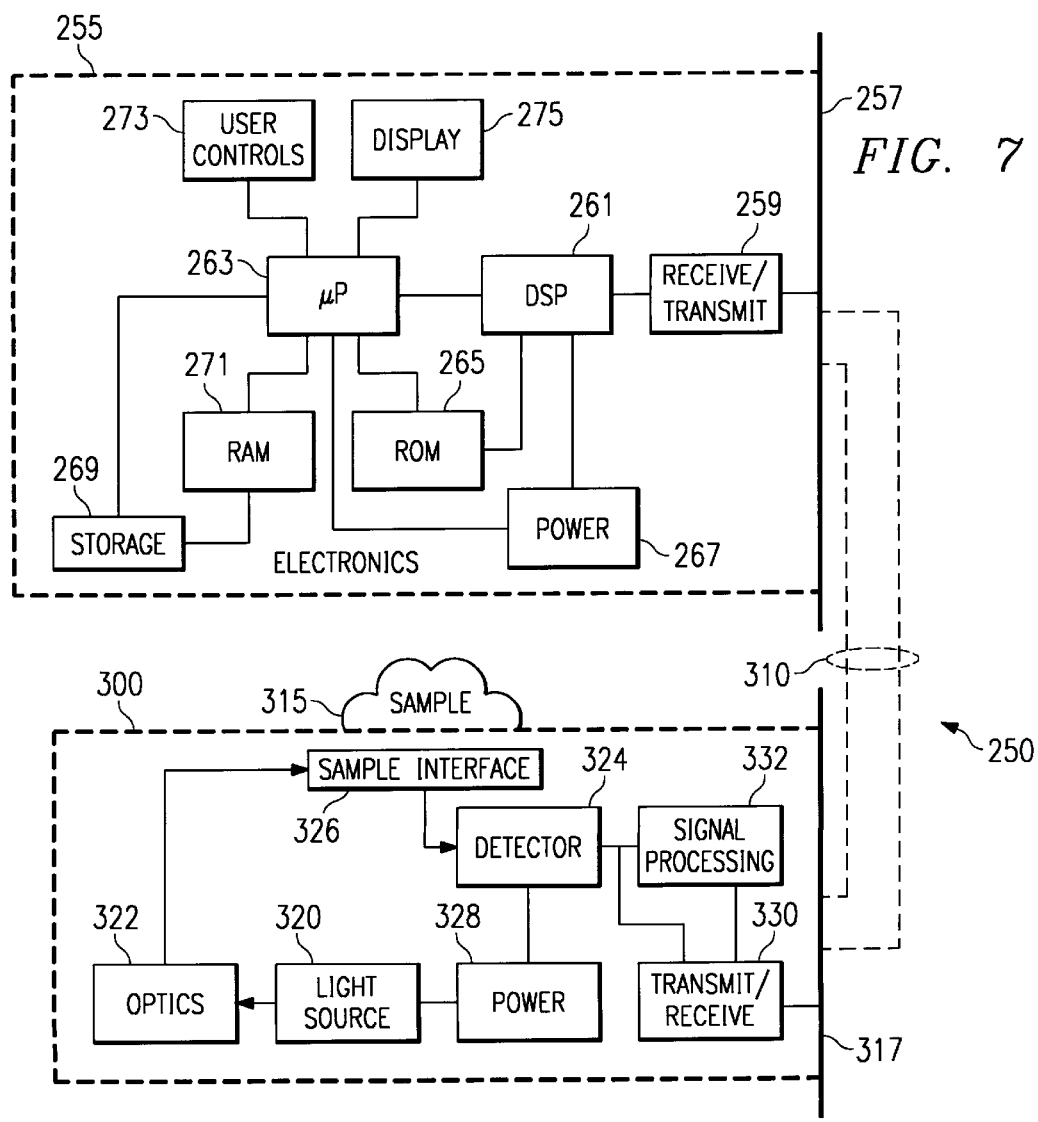

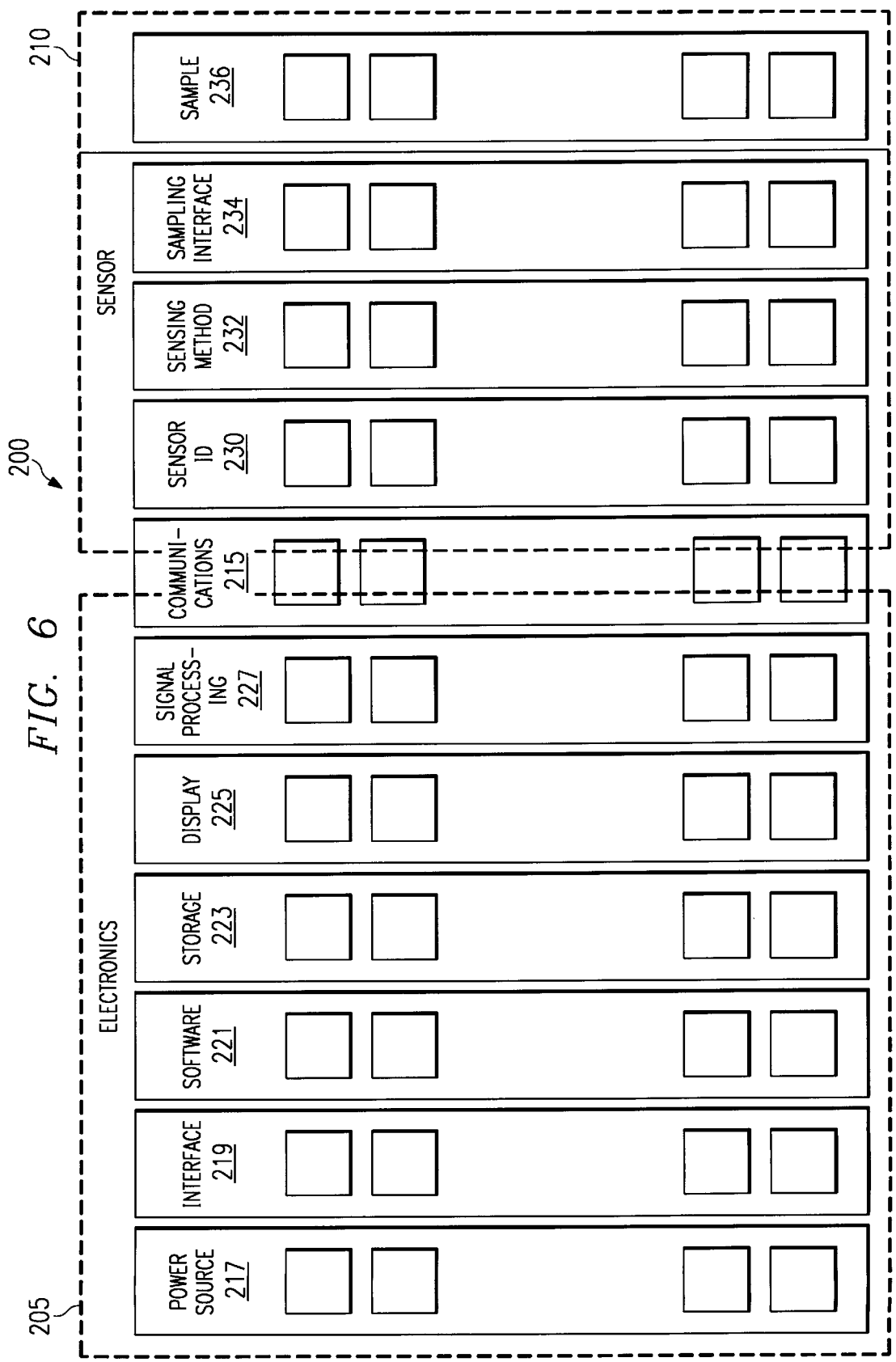

FIXED OPTIC SENSOR SYSTEM AND DISTRIBUTED SENSOR NETWORK

This application is a continuation of application Ser. No. 08/942,563 now U.S. Pat. No. 5,946,083 filed Oct. 1, 1997 which claims priority from application Ser. No. 60/027,187 filed Oct. 2, 1996.

TECHNICAL FIELD

The present invention relates in general to the field of optic sensors and more specifically to an optical sensor system and distributed architecture permitting on site sampling of a wide array of analyte samples with information storage and subsequent transfer to remote processing systems.

BACKGROUND OF THE INVENTION

Without limiting the scope of the invention, its background is described in connection with an optic based sensor system using a diverse collection of lenses, filters, detector and light components and related electronics to detect, qualify and quantify the presence of one or more sample analytes.

Optic-based sensor systems have been developed and used in the fields of chemical, (bio)chemical, biological or biomedical analysis, process control, pollution detection and control as well as others. A typical application involves the chemical coating of a thin film, cable or other article followed by excitation and measurement in the presence of a given sample of interest.

The earliest prior art systems combined a wide assortment of lenses, filters, light sources, detector component and electronics. One example is the fluorescence-based fiber optic oxygen cable sensor which uses a single high brightness Light Emitting Diode (LED) to produce an excitation signal that catalyzes the emission properties of the fluorescence coating material which interacts with the analyte sample of interest to produce a measurable difference in the emission. The material is deposited on a length of the fiber optic cable which, in turn, is emersed in the sample solution producing a measurable change in the fluorescence chemistry emission.

Another prior art system uses a prism shaped lens to direct light incoming one surface onto a second surface upon which a sample reagent or binding material has been deposited. The second surface is placed in contact with the sample which binds to or otherwise interacts with the reagent to alter the angle of refraction along the prism/sample interface. The light output is directed out the third prism surface towards a detector array that senses the angular change indicating one or more sample properties.

These earlier sensor systems had limited use in most practical field applications. The signal generator, LED, lens, filter, detector, amplifier and other components required significant amounts of work space to setup and operate. In addition, their overall high cost and immobility confined their use to the laboratory and research environment. Moreover, such systems required specialized and routine maintenance to ensure precise alignment of the optics in relation to the light sources, detector components and other sub-systems.

Recent advances in miniaturized low powered light sources and detectors has allowed the design of compact fully integrated sensors. A main feature of these miniaturized sensors is the fixed positioning of the light source, sampling surface and detector elements within a rigid solid housing. Thus, miniaturized sensors eliminate the need to transport the sample to the sensor sampling surface. Because the components are readily available the miniaturized sensors are easier to maintain and less expensive to manufacture. Also, since the optics are fixed, miniaturized sensors do not exhibit the same alignment problems of the bulkier prior art sensor systems.

Until the present invention, however, the use of the miniaturized integrated sensors in application specific hand held instruments has not been contemplated. A device that communicates with one or more sensors which are in close proximity or contact with the sample would permit distributed monitoring of environmental conditions and provide great utility.

SUMMARY OF THE INVENTION

A distributed sensor system incorporating miniaturized sensor technology wherein the optics are fixed in a self-contained housing or device platform has not been contemplated. Prior art sensing systems are too bulky and expensive for use on an in-situ basis.

As such, it is a primary object of the present invention to provide a miniaturized integrated (bio)chemical sensing system that allows field personnel to collect sample data in-situ, process, analyze, store the data, and transfer it to a local or centralized server for further analysis. The system includes a fixed optic sensor which can be drop placed in the field or throughout a facility and monitored from an electronic sub-assembly that communicates with the sensor to receive the sample data and control the sensor's operations. Multiple sensors can be monitored by using a sensor specific identifying tag which provides a location mark specific identity for each sensor.

Another object of the invention is to provide a distributed sensor architecture wherein sample data from a plurality of separate and disparate locations is transferred from the local field processors to a centralized processing system. The architecture defines a sensor system with widespread application such as in toxic waste, medical onsite diagnosis or military uses.

Another object of the present invention is to provide a sensor system that can be used as an on-site medical diagnostic tool by medical field personnel. In this regard, a device capable of resolving various cardiac markers quickly is envisioned. A blood sample is placed in contact with a sensor/sample interface which has a plurality of binding ligands thereon causing binding interactions between the ligands and specific cardiac markers. The interaction data is relayed to a local processor for analysis and onsite diagnosis which, in turn, is relayed to centralized processor for patient tracking and/or billing purposes. The field medical personnel can receive on-site diagnosis via an integrated display from either the local processing system or the centralized processor and continue treatment accordingly.

Disclosed in one embodiment, is an optical sensor system with a sensor sub-system having at least one light source, one sensor/sample surface and one detector interfaced in fixed relation to one another and an electronic sub-system that communications with the sensor sub-system to obtain sample related data. The electronic sub-system includes a signal processing means, a microcontroller, a storage area, a display, a user interface and controls. The sample data can be stored in the electronic sub-system and relayed to a centralized processing system for further analysis. The communications means between the electronic sub-system and the sensor subsystem is preferably wireless such as radio frequency or infrared. Application specific software can be included on the electronic sub-system assembly providing various user functions, options and control of the sensor sub-system.

For a more complete understanding of the present invention, including its features and advantages, reference is now made to the following detailed description, taken in conjunction with the accompanying drawings.

BRIEF DESCRIPTION OF DRAWINGS

In the drawings:

FIGS. 1 and 2B depict a prior art sensor system;

FIG. 5 is an alternative miniaturized sensor using a reflective surface and focusing surface;

FIG. 6 is a matrix level sensor system illustrating the various system options according to the invention;

FIG. 7 is a block diagram illustrating the internal arrangement of components for one embodiment of a sensor system according to the invention;

Corresponding numerals and symbols in the different figures refer to corresponding parts unless otherwise indicated.

DETAILED DESCRIPTION OF THE PREFERRED EMBODIMENT

Figure 1:
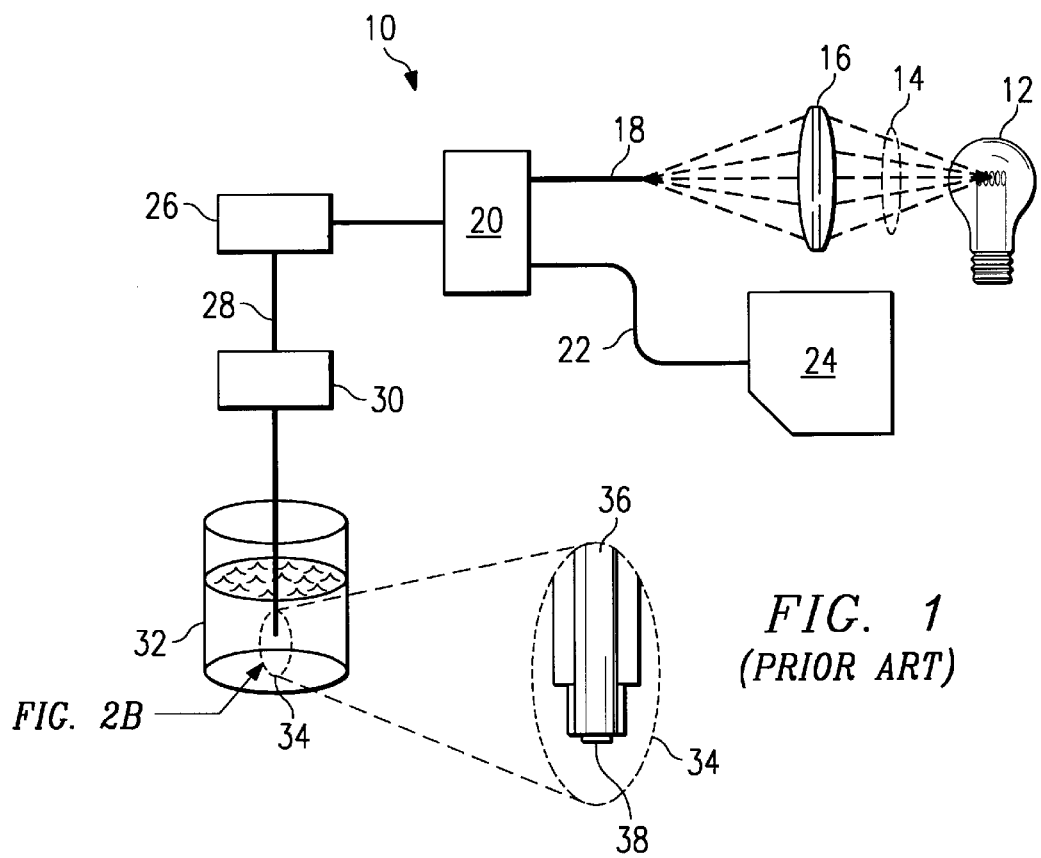

In FIG. 1, a prior art sensor system is shown and denoted generally as 10 where a light source 12 emits a light energy 14 of a predetermined intensity and wavelength known to interact with the sample 32. Various light sources may be used including a Light Emitting Diode (LED), laser, incandescent lamp, filament or other similar device. The light energy 14 is directed into lens 16 which focuses, directs and guides it into cable 18. The optic lens 16 is aligned about light source 12 and cable 18 to maximize coupling of the light 14 to other parts of the sensor system 10.

A signal splitter 20 is provided to direct a reference sample of the light signal 14 into instrument 24 via cable 22 allowing instrument 24 to track and monitor signal strength and presence. Light is coupled through connector 26 and probe length 28 into detector unit 30.

In operation, the coated fiber optic cable sensor 34 is inserted into a liquid sample 32 causing a molecular interaction of the chemistry coat with the sample. Thus, sensor 34 may be coated with a fluorescence emitting chemical which when exposed to the sample 34 alters the fluorescence emission. As shown, the sensor 34 has a core 36 which a molecular assay deposited thereon. A sample reading of the radiated emission light energy is received by instrument 30, via sensor 34 and probe end 38 so that the presence of sample 32 is confirmed by the detector 30. Likewise, sensor system 10 can be configured to detect gases, solids and/or other molecular property of a solution or compound depending on the sample/chemistry combination employed.

FIG. 1 illustrates a sensing system 10 wherein the optics 16 are not immobilized or fixed in stationary positions with respect to the electronics and where the electronics 20, 24, 26 and 30 are physically coupled with cables—a prior art sensor system of the type used in laboratory and research environments. The bulk and expense of such sensor systems lead to the development of more integrated miniaturized sensors as illustrated in FIGS. 2, 3, 4 and 5.

Figure 2:
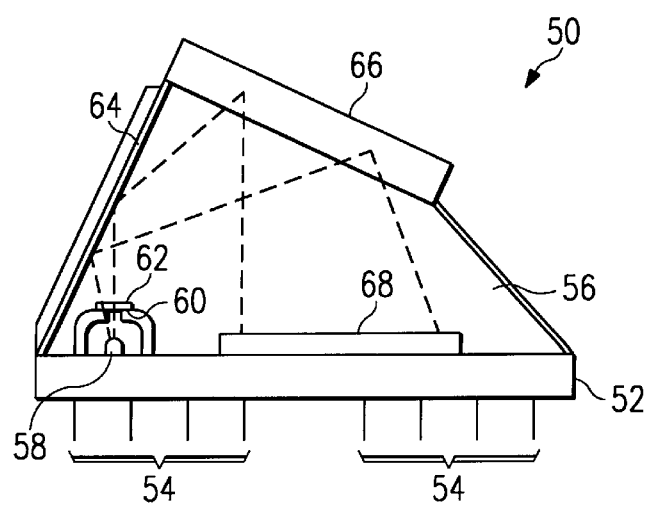
FIG. 2 is a side profile view of a miniaturized integrated surface plasmon resonance sensor.

For example, in FIG. 2 an integrally formed Surface Plasmon Resonance ("SPR") sensor 50 is shown. A substrate 52 provides a device platform to which a light transmissive housing 56 is coupled. A light source 58 is preferably located above or within the substrate 52 and has an aperture 58 there over allowing light to pass. A polarizer 62 is located near the aperture 58 to polarize passing light which, in turn, continues through housing 56 and strikes a SPR layer 64 which is preferably formed on an exterior surface of the housing 56. The SPR layer 64 may be deposited or placed on a glass slide or the like. This configuration achieves an optical surface phenomenon that can be observed when the polarized light is totally internally reflected from the interface between the layer 64 and the sample of interest (not shown in FIG. 2).

As shown, a mirrored surface 66 directs the reflected light onto a detector array 68 which senses illumination intensity of the reflected light rays. For optical radiation, a suitable photodetector 68 is the TSL213, TSL401, and TSL1401, with a linear array of resolution n×1 consisting of n discrete photo sensing areas, or pixels. Light energy striking a pixel generates electron-hole pairs in the region under the pixel. The field generated by the bias on the pixel causes the electrons to collect in the element while the holes are swept into the substrate. Each sensing area in the photodetector 68 thereby produces a signal on an output with a voltage that is proportional to the intensity of the radiation striking the photodetector 68. This intensity and its corresponding voltage are at their maxima in the total internal reflection region.

A lead frame 54 is coupled to the opposite side of the substrate 52 and provides a signal pathway from the detector 68 output to the external world.

Figure 3:
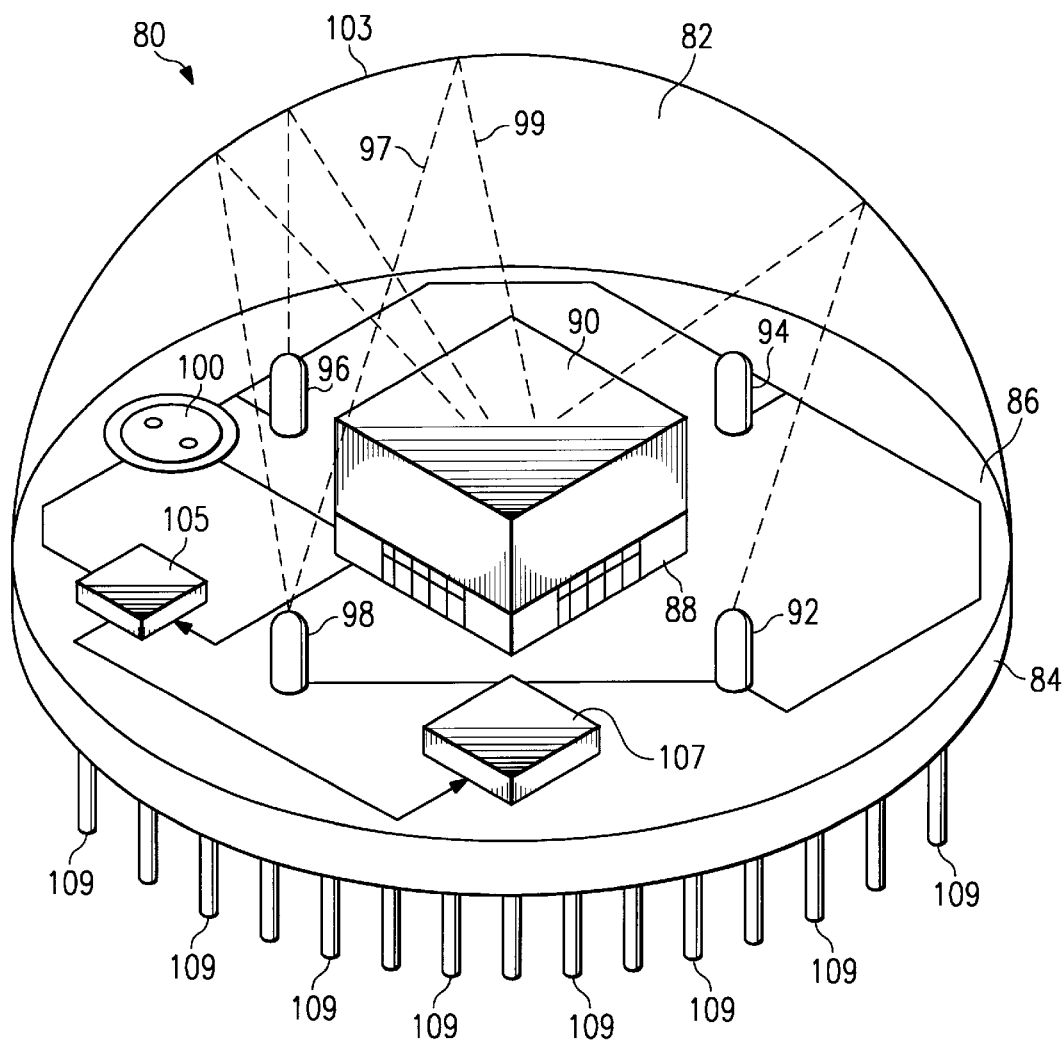
FIG. 3 is perspective view of a miniaturized integrated fluorescence-based sensor.

In FIG. 3, a miniaturized integrated fluorescence sensor 80 is shown having a hemispherical dome-shaped housing 82 which extends from the upper surface 86 of platform 84 forming a substantially encapsulating structure.

A light photodetector 88 is coupled to the upper surface 86 at a substantially central location within the housing 82. The photodetector 88 may be a light-to-voltage or light-to-frequency converter, such as the TSL250 or TSL230, respectively, thereby producing an output signal with a voltage proportional to the intensity of the radiation energy striking the photodetector 88.

Directly overlying photodetector 88 is filter 90 element which blocks light from the photodetector 88 outside a certain wavelength spectrum. Four (4) light sources 92, 93, 94 and 95 are coupled to the upper surface 86 surrounding the photodetector 88 at substantially equidistant positions from the center of the platform 84 and symmetrically arranged about and within the housing 82.

A power source 100 is also coupled to the upper surface 86 and operably coupled to the various active components of the sensor 80 including photodetector 88, light sources 92, 94, 96 and 98 among others providing power to all the electro-optical components within the housing 82 and allowing the sensor 80 to operate without an external link to an outside source of power.

Light emissions 97 and 99 illustrate the operational aspects of the sensor 80. Light 97 from light sources 92 94, 96 and 98 is incident to upper surface of the filter 90 and the platform 84 where it is absorbed. The fluorescent chemistry 103 on the outer surface of the housing 82 interacts with the ambient sample(not shown) and produces a change in the fluorescence emission which travels toward the photodetector 88. The light absorbent filter 90 blocks out unwanted energy wavelengths which are outside the emission spectra of interest.

The A/D converter 105 receives an analog signal from photodetector 88 producing a corresponding digital output signal for digital storage and analysis. A/D converter 105 is coupled to upper surface 86 of the platform 84 and embedded within housing 82. Likewise, signal processing circuit 107 may be provided and coupled to platform 86 and communicably interfaced to the A/D convertor 105 to receive the output digital signal relating to the sample in question.

Data from signal processing circuit 107 may be sent to a remote processing system via interface 109 coupled to the bottom surface of the platform 84. A display may also be a provided on the exterior of the sensor 80 and used to render visual feedback to the user indicative of the sample under test.

Figure 4:
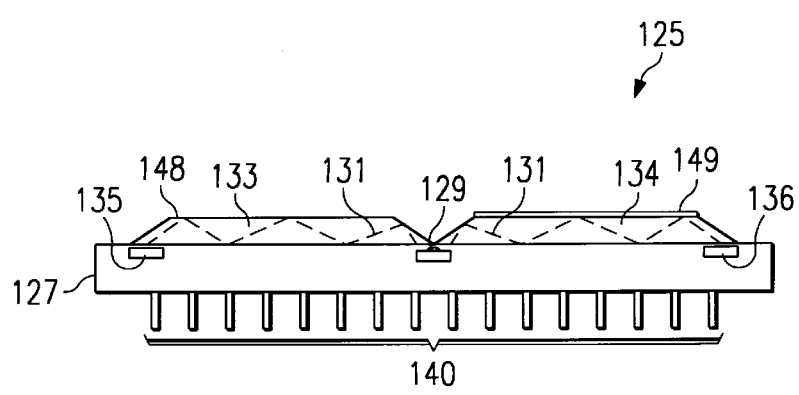
FIG. 4 is a side view of an miniaturized integrated light transmission sensor.

In FIG. 4, a miniaturized light transmission sensor is shown and denoted as 125. Sensor 125 is a self-contained light transmission device having a platform 127 with at least one light source 129 which generates a light signal 131 optically coupled via light guides 133 and 134 towards photodetectors 135 and 136. As shown, one of the light guides 134 has an upper surface 149 which comprised a molecular coat known to interact with a sample of interest.

At least one light source 129 is positioned about platform 127 with the photodetectors 135 and 136 coupled on opposite sides of light source 129 and disposed to receive light 131 traveling through light guides 133 and 134, respectively. Thus, when the sample of interest comes in contact with surfaces 149, the optical properties at the interface are measurably altered. This change is detected at photodetector 136 and may be analytically compared to the reference output of detector 135. As with other integrated sensor configurations, a lead frame 140 is provided as an interface between the internal sensor components and the outside world.

Yet another configuration of an SPR sensor 150 is shown in FIG. 5 wherein the shape of the housing 155 and mirror 160 provide some added advantages. Light 157 from light source 153 is polarized by polarizer 159 which diverges into the light transmissive housing 155 in the direction of planar mirror 162 which is disposed so that the plane thereof is not normal to the direction of the polarized radiation 158.

The diverging polarized light is directed toward a curved mirror 160 disposed on a curved exterior surface of the housing 155. When the mirror 160 is concave, the shape causes the radiation reflected therefrom to converge at the SPR layer 170 which can comprise a thin layer of conductive material such as copper, silver or gold having a substantially uniform thickness. Layer 170 is preferably planar although other configurations, such as convex or concave or otherwise featured may be used. The reflected radiation reaches detector array 175 wherein the intensity of the light reflected is resolved. A lead frame 177 is provide and secured to the housing 155 providing a signal pathway from the detector 175 to the outside world.

The invention relates to a sensor system using fixed optic miniaturized integrated sensors such as those illustrated in FIGS. 2, 3, 4 and 5 which provides numerous advantages over the prior art sensor systems. In that respect, FIG. 6 is a feature level matrix of a sensor system according to the invention and is denoted generally as 200. Sensor system 200 has an electronic sub-system 205 that is communicably interfaced to a fixed optic sensor sub-system 210 which includes all the necessary optics and photosensing electronics necessary for (bio)chemical sensing.

A communications means 215 is provided to allow the sensor sub-system 210 and electronic sub-system 205 to communicate via a wide array of communications formats. For example, communications means 215 may comprise a plurality of signal paths or wires connecting the sensor 210 to the electronics 205 which define physical signal pathways. Fiber optic cabling, twisted pair wiring, network coax or other physical connections mediums may be used. Also, a communications protocol such as serial and/or parallel data transfers between the sensor 210 and the electronics 205 may be employed.

Likewise, communications means 215 may take the form of wireless communications system between the two sub-systems 205, 215 including radio frequency, infrared, satellite or other broadcast signal. Other contemplated communications means 215 are point-to-point, on demand, secured transmissions or other custom communications protocol, all of which are well known to those skilled in the art.

On the electronics side 205 of the sensor 200, various functional features are provided and operably coupled to each other according to the numerous contemplated embodiments which will become apparent to those skilled in the art. A source of power 217 is provided to activate and run the various active components of the sub-system 205. Power source 217 can be solar, battery driven, alternating current, direct current, a generator or a remote power source, according to the invention. An interface 219 gives the user input and functional control of the sub-system 205 depending on the specific application of the sensor 200.

A keyboard, control pad, mouse, touch screen or other mechanical means of control and input may form part of the interface 219. Likewise, the interface 219 may be implemented as a remote control subassembly of the electronic sub-system 205 which is operably coupled to the sensor system 200 for remote use and operation. In yet another contemplated embodiment, the interface 219 comprises a switch or button which the user activates in order to command sensor functions.

Software 221 can be maintained on the electronic sub-system 205 to control the various sensors functions and processes according to the specific sensor application. In one embodiment, the software 221 is controlled by the user interface 219 allowing the user to view and display data results via display 225 and/or otherwise manipulate the sample related data as obtained by the sensor sub-system 210.

For example, the user can use interface 219, software 221 and display 225 to determine when the sample of interest is detected by the sensor sub-system 210. The data can be manipulated, graphed or otherwise analyzed depending on software 221 features. A help system may also be included in the software 221 to assist the user with various system 200 features. The software 221 can be used to store, retrieve or transmit data and/or commands to the sensor or a remote processing system according to the invention.

Also shown is a storage area 223 that can be a hard disk, floppy disk or other magnetic means of storage or a chip-based storage device such as DRAM, EEPROM, flash memory, ROM or other similar components. Storage area 223 provides a space where sample related data, test history, calibration information or other similar data can be stored.

A display 225 can be included and operably coupled to the various components of the electronic sub-system 205. In a simple embodiment of the sensor 200, display 225 comprises one or more LEDs which are actuated at times when the sensor 210 detects the presence of the particular sample of interest. In other embodiments, display 225 comprises a liquid crystal display (LDC), a monitor or CRT which provides alpha numeric output relating to the sample of interest. Other contemplated display means 225 include hard copy, digital or analog signal outputs, audio alarm, synthetic voice, pager or projection among others.

Also shown is a signal processing means 227 on the electronics side 205 of the sensor system 200 which converts, processes, assembles and otherwise manipulates the data received from the sensor sub-system 210. In one embodiment, the sensor 210 generates a digital bit-stream data output related to the sample of interest which is relayed via communications means 215 to the electronics sub-system 205 and received by the signal processing unit 227 for further analysis. The data is the output of an analog-digital convertor of the sensor 210 platform which is integrally molded on the sensor platform.

In another embodiment, the output from the sensor 210 is a modulated carrier relating the sample of interest that is transmitted to the signal processing means 227 via a wireless communications mode 215. For example, an RF transmitter can be incorporated in the sensor 210 as part of communications 215 and used to modulate an airborne signal which is received by the communications side 215 of the electronics sub-system 205 and transferred to the signal processing unit 227 for demodulation and further analysis.

Those of skill in the art will recognize that a wide variety of signal processing methods are envisioned. For example, the signal processing means 227 can be an onboard digital signal processor of the type readily available in industry. Also a microcontroller, microprocessor or other high scale integrated circuit can be used to analyze the incoming data from the sensor 210. Other options include a data analyzer, calculator or application specific integrated circuit.

Turning now to the sensor side 210 of the sensor system 200, FIG. 6 shows that a sensor ID 230 such as a barcode, RF tag or other sensor specific identifier is used to identify the specific sensor in question. This provides a sensor system that is location and/or sample specific depending on the particular sensor application. Thus, a sample specific sensor can be so labeled via sensor ID 230 permitting electronic sub-system 205 to determine the location of the sensor and, if desired, the specific sample which the individual sensor is designed to detect. In another embodiment, a plurality of sensors can be placed in a remote field, facility, or combination thereof and the location and sample type determined via sensor ID 230.

Those skilled in the art will appreciate that by including a sensor ID 230 on or in the sensor 210 platform, a distributive network of sensors can be obtained. Accordingly, a plurality of sensor ID 230 types are envisioned, including a barcode, radio frequency tag, color code, a label, electronic signature or memory stored identifier.

The sensor method 232 of the sensor subassembly 210 depends primarily upon the sensor configuration including those illustrated in FIGS. 2,3,4 and 5. Thus, surface plasmon residence, fluorescence-based, critical angle and light transmission configurations are suitable sensor 210 types. Others include chemiluminescence, colorimetric, visible and infrared spectroscopy, absorption, phase, photometry and others (bio)chemical sensing methods, all of which are known by those skilled in the art.

The sensor sub-assembly 210 has a sampling interface 234 which defines the barrier between a sensor 210 surface and the sample in question. For example, the sensor 210 can be manually introduced into the sample to make contact along a surface or other region of the sensor platform. Other sampling methods include fluidics, wherein the liquid sample is allowed to run over the sensor 210, vapor transport or osmosis for gas samples or the use of a flow cell to hold the sample within a contained region. In one contemplated use of the invention, the sensor 210 is used in-situ and the electronic sub-system 205 is held at distance from the sensor sub-system 210.

As shown, the sample 236 is kept in contact or close proximity to a sensor sub-system 210 surface. Since the sensor system 200 has widespread application, the sample 236 can be a chemical, biological, solid, gas, plasma or a combination thereof.

In short, a sensor system 200 has been defined that incorporates miniaturized sensor technology having fixed optics inside a rigid, self-contained sensor platform or housing to eliminate the optical misalignment problems found with prior art sensors. The sensor 200 combines an assortment of communications means 215 which permits the integrated miniaturized sensor 210 to be drop placed at or near the sample of interest without interference from field personnel.

Turning now to FIG. 7, a block diagram of a wireless sensor system 250 according to one aspect of the invention is shown. FIG. 7 shows that electronics 255 of sensor 250 is separate and apart from the integrated miniaturized sensor 300. A communications pathways 310 is preferably an radio frequency transmission path wherein data and information between the electronics 255 and the sensor 300 is transferred on a modulated carrier. Pathway 310 may also be infrared or other form of signal broadcast permitting wireless transfer of data and information.

Within the electronics 255, the various functional components and devices used to receive, analyze, store and manipulate the data from the sensor 300 are found. The electronics 255 are enclosed in housing 257 which contains the various components in place providing a self-contained unit. A receiver/transmitter 259 is provided for coupling data from the sensor 300 to a digital signal processor 261 which, in turn, receives the sample data as an analog signal and converts it to its corresponding digital format.

A micro controller 263 is communicably coupled to the digital signal processor 261 and performs the various functional operations of the electronic sub-system 255. Likewise, the microprocessor 263 and digital signal processor 261 can be preprogramed to be internally maintained routines on ROM 265 which, in one embodiment, are loaded as power 267 is applied during initial startup. This provides a completely isolated device 255 which can operate without a remote source of power.

The data received from the signal processor 261 is manipulated and stored in storage area 269 which, in one embodiment, comprises a static memory area which assures its contents are maintained, even during loss of power. Also provided is a dynamic memory area 271 which can be used by the microprocessor 263 as a work space during device operation. As shown, the microprocessor 263 is controllably linked to user controls 273 and display unit 275. In one embodiment, the display 275 is a liquid crystal display capable of alpha numeric representation.

On the sensor 300 side of sensor system 250, FIG. 7 shows that the sample of interest 315 is placed in contact with sensor housing 317. Within the sensor 300 is found light source 320, light optics 322, sample interface 326 and detector unit 324 which are interfaced in fixed relation to one another inside the enclosure 317. This eliminates the alignment problems found in the prior art sensors, providing a self-contained unit which is ideal for field use applications.

In various embodiments of the sensor 300, a self-contained power source 328 and signal processor unit 332 are provided which operate according to their functions as appreciated by those skilled in the art. Also, a transmitter receiver 330 is operably coupled to the sensor platform 317 and provides the communication functions and capabilities of the sensor 300.

Figure 8:
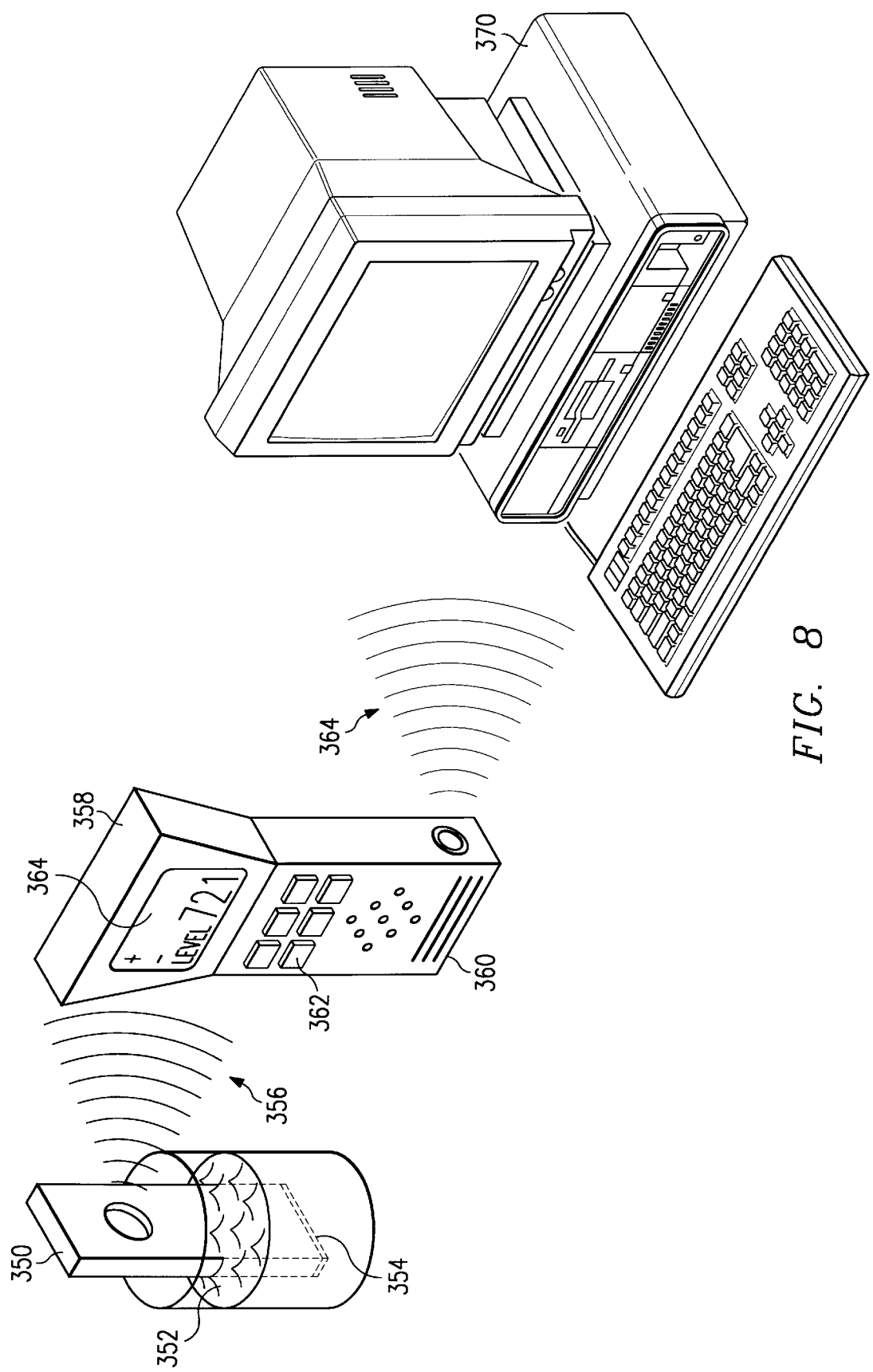
FIG. 8 depicts a practical sensor application according to one aspect of the invention.

Turning now to FIG. 8, a practical application of the invention is shown wherein a miniaturized integrated sensor 350 is immersed in a liquid sample 352 making contact with a sensor surface 354 to produce an interaction at the sampling interface between the sample 352 and the sensor 350. As shown, the presence of the liquid sample 352 is detected by the sensor 350 and communicated 356 to a hand held unit 358 through one or more known wireless communication methods 356.

The hand held unit 358 consists of an instrument enclosure 360 having user controls 362 and display unit 364 which renders visual information about the sample 352 to the user. The sample related data can be stored, processed, analyzed or otherwise manipulated and transmitted 364 to a remote processing unit 370. As shown, the interface between the instrument 358 and remote processing unit 370 is wireless although it should be understood that a physical connection may also be used.

Figure 9:
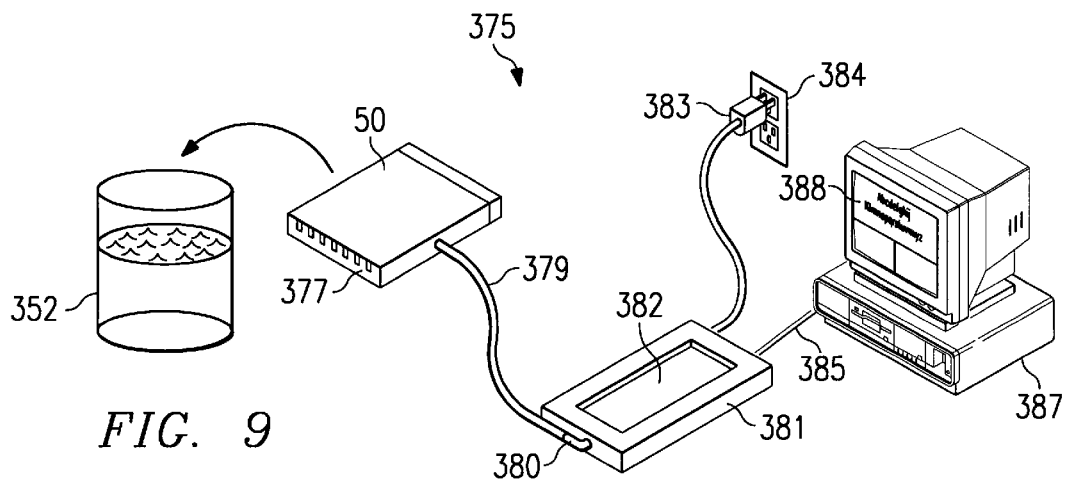
FIG. 9 depicts an integrated sensor kit according to another aspect of the invention.

An integrated sensor kit 375 is illustrated in FIG. 9 wherein an SPR sensor 50 is used to analyze the (bio) chemical properties of liquid sample 352 by direct emersion. The sensor 50 is coupled to module 377 which provides the interface between the sensor 50 and cable 379. Cable 379, in turn, provides a signal pathway from the sensor 50 detector to blackbox 381 via interface 380. A communications protocol may be used to handle the handshaking and data transfer between the sensor 50 and the blackbox 381 along cable 379.

Inside the blackbox 381 are found the various electronics 382 such as microprocessor 263 and analog to digital convertor 261 which perform the various signal processing and algorithmic functions according to the invention. Adapter 383 is plugged into socket 384 and used to provide power to the various active components inside the blackbox 381. The processed data can be transferred to processing system 387 which can be a desktop computer, workstation or other similar computing means. Cable 385 provides the interface between the blackbox 381 and system 387 using a standard communications protocol such as RS-232 or parallel.

A software application program 388 can be executed on system 387 and used to analyze the sample 352 related data received from the blackbox 381. For example, a graph can be plotted indicating the reflective index between the sensor surface and the sample 352 as a function of time, light intensity or other variable. Other results may also be obtained depending on the particular application as is appreciated by those skilled in the art.

Figure 10:
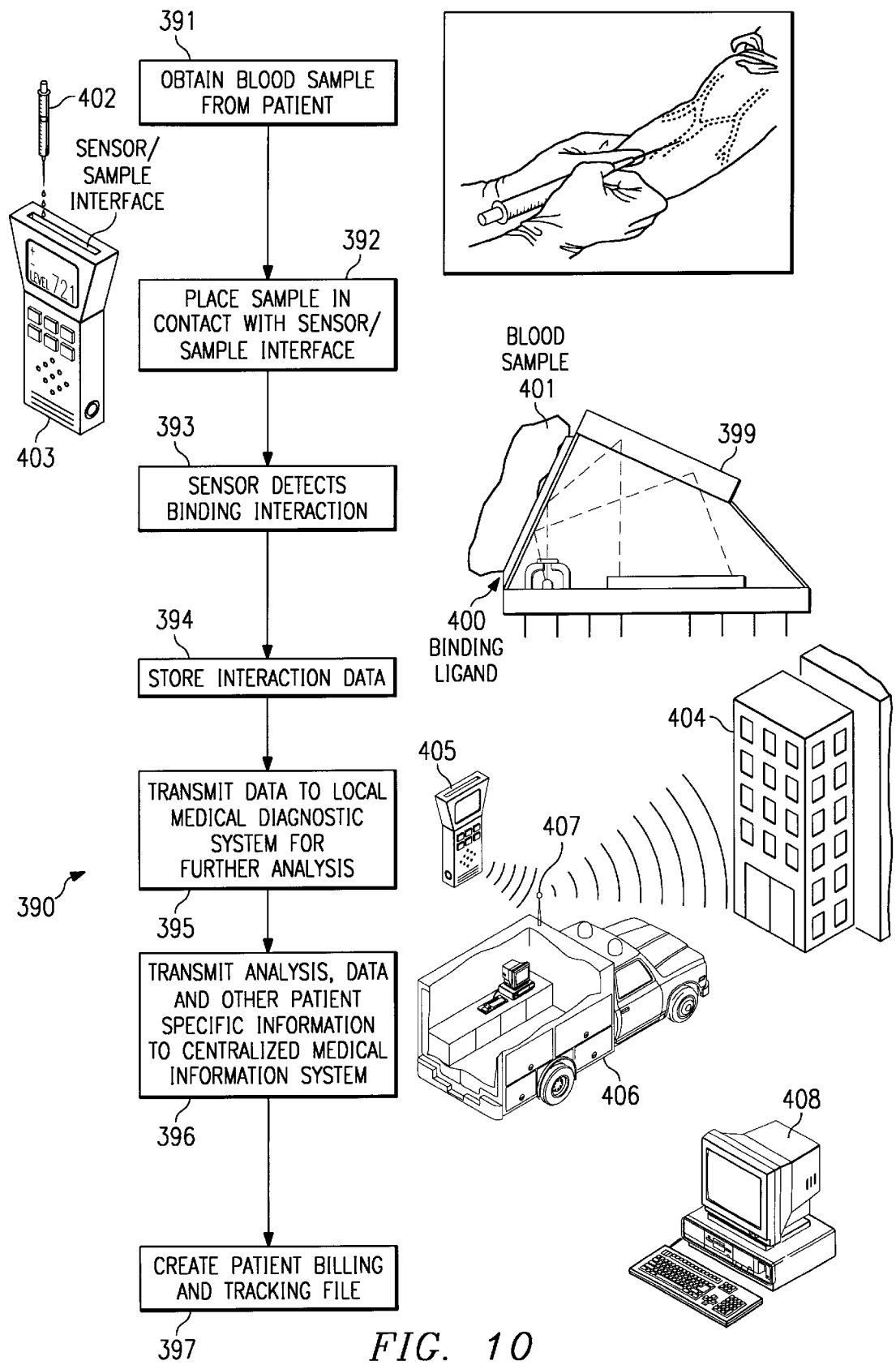
FIG. 10 illustrates an alternative field application of a sensor system according to one aspect of the invention.

In FIG. 10, a medical diagnosis and point-of-care application using a sensor system according to the invention is illustrated and denoted as process 390. Process 390 allows medical personnel to obtain blood samples from patients on an on-site basis 391 and thereby permit qualitative and/or quantitative analysis about the patient without immediate transport to a hospital or other medical facility 404.

The medical personnel obtains the sample 391 and places it in contact with the sensor sample interface 392 permitting one or more binding ligands along a sensor sample surface to interact with the blood sample 401. An SPR (bio)chemical sensor of the type illustrated in FIG. 2 has been found useful for this purpose. The sensor detects binding interactions 393 between the surface and the sample and store the interaction data 394 in an internal storage area 269 for future retrieval and/or processing or for download to a larger processing system.

Likewise, the interaction data can be transmitted to a local medical diagnostic system for further analysis 395. In one embodiment, the local diagnostic system is kept onboard an ambulance 406 which communicates with the sensor 405 providing medical personnel with on-site diagnosis and treatment information. From there, the sample data, diagnosis and patient information can be transmitted to a centralized medical information system at the medical facility 404, permitting patient billing and tracking prior to the arrival of the patient at the care facility 396.

In one form of the invention, a sensor system capable of detecting the presence of various cardiac markers is provided to diagnose atypical chest pain on a point-of-care basis. Using an SPR sensor 50, the SPR layer 64 can be coated with binding ligands 400 known to bind with various cardiac indicative markers. These markers include Creatine Kinase-MB, Myoglobin, Cardiac Troponin T, Cardiac Troponin I and Glycogen Phosphorylase Isoenzyme BB. As is known by those skilled in the art, these cardiac markers are present in blood samples as indicative of Acute Myocardial Infarction (AMI) which occurs when a lack of oxygen causes the death of a heart muscle.

Thus, the present invention envisions a sensor system that allows rapid detection of an AMI occurrence as opposed to some other coronary event allowing the on-site medical personnel to manage the clinical event quickly and appropriately.

Figure 11:
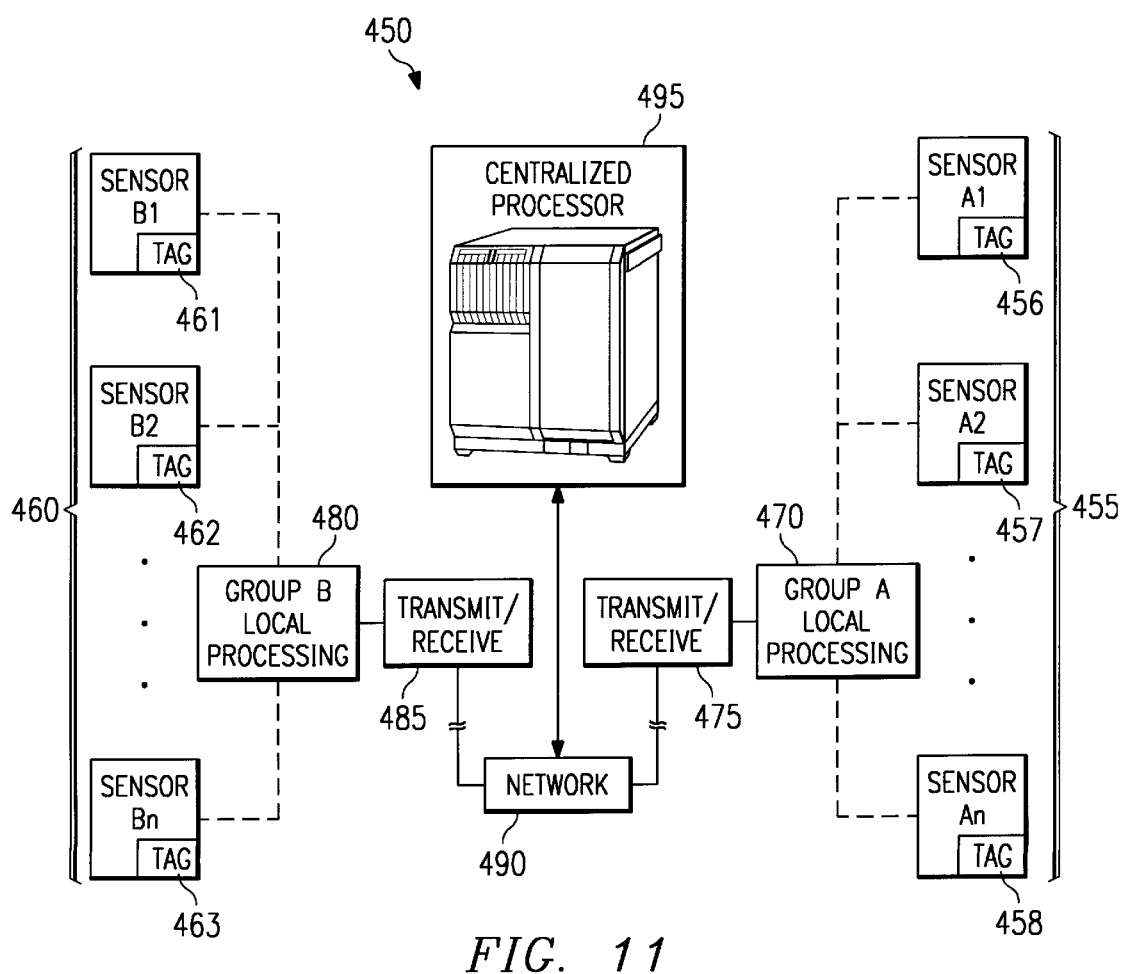
FIG. 11 is a block diagram illustrating a distributed sensor network and architecture according to one aspect of the invention.

Turning now to FIG. 11, an architecture for a distributed sensor system according to the invention is shown and denoted generally as 450. A sensor array 455 is shown comprising a plurality of sensors A-1, A-2 through A5 N. Each sensor in the sensor array 455 has an individual ID tag 456, 457, and 458 to distinguish it from other sensors and designate them as belonging to the array 455.

A local processing system 470 monitors the placement, location and data content of each sensor in the array 455. In one embodiment, the local processing system 470 is a hand held portable instrument such as the one illustrated in FIG. 8 (358) which field personnel can take with them to the sample site.

Likewise, each one of the individual sensors and the sensor array 460 has an individual tag associated with it and the sample data collected by each sensor can be transmitted to the Group B local processing system 480 where it is stored, processed, analyzed and/or otherwise manipulated.

As shown, the data from the Group A local processor 470 can be transmitted 475 to a more centralized network system 490. In the same way, the data from the Group B local processor 480 is transmitted 485 to the network 490. As described above with respect to FIG. 6, the communications mediums can be many, including radio frequency, satellite, infrared or physical link. The network 490 can transmit the distributed data to a centralized processor 495 which can be a personal computer workstation, mini-computer, mainframe or other similar system depending on the specific application.

In short, the present invention envisions a distributive (bio)chemical sensing system with widespread application. For example, a regional or nationwide medical information and patient tracking system is encompassed wherein patient specific test data, medical history and preventative health care data is managed on a regional or national basis.

Likewise, the present invention has application in military and toxic waste applications wherein a plurality of sensors and sensor arrays are monitored to track the presence of harmful substances in an open field, a facility or other region. Other uses and applications will become apparent to those skilled in the art.

Various modifications of the illustrative embodiments as well as other embodiments of the invention will be apparent to persons skilled in the art upon reference to the description and it is therefore intended that the appended claims encompass any such modifications or embodiments.

What is claimed is:

1. A fixed optic sensor system for detecting one or more (bio)chemical properties of a sample analyte comprising:
   a sensor sub-system comprising an integrated miniaturized sensor having a sensor/sample surface in contact with the analyte and at least one light source and one detector interfaced in fixed relation to said sensing surface;
   an electronic sub-system comprising an on-board signal processor, storage area, user interface and display functionally interfaced with each other to process, store and display information relating to the sample analyte; and
   a communications sub-system communicably coupling the sensor sub-system to the electronic sub-system for receiving and transmitting sample data.

2. The sensor system according to claim 1 wherein said electronic sub-system further comprises:
   an on-board power source operably coupled to said processor, storage area, user interface and display for providing operation power;
   a static memory area operably coupled to said processor; and
   software embedded in said static memory area and providing a plurality of user control and sample related functions for operating the electronic sub-system and for analyzing and displaying sample related results.

3. The sensor system according to claim 2 wherein said processor is an on-board microprocessor circuit and the system further includes an on-board analog to digital convertor circuit communicably coupled to said sensor sub-system via the communications sub-system for receiving sample related analog data, converting it to its digital bitstream form and relaying it to the microprocessor circuit for further processing.

4. The sensor system according to claim 1 wherein said communications sub-system is a wireless radio frequency communications system.

5. The sensor system according to claim 2 wherein said sensor sub-system further includes a sensor identification tag.

6. The sensor system according to claim 2 wherein said electronics sub-system is self-contained in a hand held instrument enclosure.

7. The sensor system according to claim 2 wherein said sensor sub-system is a surface plasmon resonance sensor having an SPR layer.

8. The sensor system according to claim 2 wherein said sensor sub-system is a fluorescence-based sensor.

9. The sensor system according to claim 7 wherein said electronic sub-system is self-contained in a hand held instrument enclosure and wherein said SPR layer is coated with one or more binding ligands.

10. The sensor system according to claim 2 further including a remote processing system communicably interfaced with said electronics sub-system for receiving sample related data, said remote processing system operably equipped to analyze, store and process said data and control the operation of said sensor sub-system.

11. An optically aligned sensor system for detecting the presence of one or sample analyte properties comprising:
    a miniaturized integrated sensor enclosed in a light transmissive housing having at least one surface in contact with said analyte and at least one light source and one detector fixed within said housing;
    an electronic sub-system communicably interfaced to said sensor for receiving and transmitting sample related data, said sub-system having an on-board signal processor, static memory area containing a plurality of application specific program segments, a dynamic memory area, a display and a user interface; and
    a communications sub-system coupling said sensor to said electronic sub-system.

12. The sensor system according to claim 11 wherein said electronic sub-system is contained in a hand held instrument enclosure.

13. The sensor system according to claim 12 further including a remote processing system communicably coupled to said electronic sub-system via a wireless transmitter/receiver.

14. The sensor system according to claim 11 wherein said sensor is a surface plasmon resonance sensor and further including a plurality of cardiac marker binding ligands deposited on said surface of said housing.

15. The sensor system according to claim 11 further including an on-board power source coupled to said signal processor, said static memory area, said dynamic memory area and said display for providing operating power.

16. The sensor system according to claim 11 wherein said communications system is a radio frequency transmitter/receiver.

17. The sensor system according to claim 11 wherein said display is a liquid crystal display.

18. The sensor system according to claim 11 wherein said sensor is a miniaturized fluorescence-based sensor.

19. A method of detecting a sample analyte using a fixed optic sensor system comprising a sensor sub-system that communicates with an electronic sub-system via a wireless communications, said method comprising the steps of:
    placing the sample in contact with the sensor sub-system;
    directing light towards the interface between the sample and the sensor;
    measuring the intensity of the light emerging from the interface between the sample and the sensor to produce an analog signal relating to the concentration of the sample;
    converting the analog signal to a corresponding digital bitstream sequence;

transmitting the bitstream sequence to the electronic sub-system for further processing;

processing the sequence to obtain analytical information about the sample to obtain sample analyte results; and displaying the results on an on-board display of the electronic sub-system.

\* \* \* \* \*